US008633244B2

(12) United States Patent
Dierker

(10) Patent No.: US 8,633,244 B2
(45) Date of Patent: *Jan. 21, 2014

(54) COSMETIC COMPOSITIONS COMPRISING ESTERS BASED ON 2-PROPYLHEPTANOL

(75) Inventor: Markus Dierker, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,344

(22) Filed: Sep. 12, 2012

(65) Prior Publication Data

US 2013/0004555 A1    Jan. 3, 2013

Related U.S. Application Data

(62) Division of application No. 12/597,577, filed as application No. PCT/EP2008/003066 on Apr. 17, 2008, now Pat. No. 8,288,436.

(30) Foreign Application Priority Data

Apr. 26, 2007  (EP) .................................. 07008475

(51) Int. Cl.
*A61K 31/325* (2006.01)
*C07C 69/00* (2006.01)

(52) U.S. Cl.
USPC .......................................... 514/544; 560/64

(58) Field of Classification Search
USPC .......................................... 514/544; 560/66
See application file for complete search history.

(56) References Cited

U.S. PATENT DOCUMENTS

| 2,921,089 | A | 1/1960 | Hagemeyer et al. |
| 5,627,056 | A | 5/1997 | Casey et al. |
| 5,840,943 | A | 11/1998 | Ansmann et al. |
| 2004/0138358 | A1 | 7/2004 | Koch et al. |
| 2005/0019353 | A1 | 1/2005 | Prinz et al. |
| 2005/0089497 | A1 | 4/2005 | Prinz et al. |
| 2006/0275234 | A1 | 12/2006 | Dierker et al. |
| 2007/0027244 | A1 | 2/2007 | Schar et al. |
| 2009/0182046 | A1 | 7/2009 | Dierker et al. |

FOREIGN PATENT DOCUMENTS

| DE | 10160681 | 6/2003 |
| DE | 10160682 | 6/2003 |
| DE | 10305562 | 8/2004 |
| EP | 0766661 | 4/1997 |
| EP | 1415978 | 9/2003 |
| WO | WO-2006/097235 | 9/2006 |

OTHER PUBLICATIONS

"Benzene—Aromatic Compounds", <http://www.uea.ac.uk/~c286/aromaticnotes.htm> Feb. 10, 2004 (Wayback Machine), 5 pgs.
Kirk-Othmer, "Diuretics To Emulsions", *Encyclopedia of Chemical Technology*, 3rd Edition, vol. 8 1979, 5 pgs.
"Office Action from corresponding U.S. Appl. No. 13/611,388", dated Nov. 27, 2012, 9 pgs.
Office Action from U.S. Appl. No. 13/611,388, May 2, 2013, 10 pages.

*Primary Examiner* — Shirley V Gembeh
(74) *Attorney, Agent, or Firm* — Sevilla Whitney LLC

(57) ABSTRACT

The invention relates to the use of esters of 2-propylheptanol with benzoic acid and/or benzoic acid derivatives in cosmetic and/or pharmaceutical preparations. The compounds are distinguished by their particularly light sensory impression.

7 Claims, No Drawings

US 8,633,244 B2

COSMETIC COMPOSITIONS COMPRISING ESTERS BASED ON 2-PROPYLHEPTANOL

CROSS-REFERENCE TO RELATED APPLICATIONS

This application is a divisional application of U.S. patent application Ser. No. 12/597,577, filed Oct. 26, 2009, which is the National Phase entry of PCT/EP08/03066, filed Apr. 17, 2008, which claims priority to EP 07008475, filed Apr. 26, 2007, the entire contents of which are incorporated herein by reference in their entirety.

FIELD OF THE INVENTION

This invention relates to the use of esters of 2-propylheptanol with benzoic acid and/or benzoic acid derivatives in cosmetic and/or pharmaceutical preparations, to specific esters and to a process for their production.

PRIOR ART

Cosmetic hair and skin-care emulsions are expected by the consumer to satisfy a number of requirements. Apart from the cleansing and caring effects which determine the particular application, importance is attributed to such diverse parameters as highest possible dermatological compatibility, good lipid-layer-enhancing properties, elegant appearance, optimal sensory impression and shelf life.

Besides a number of surfactants, cosmetic hair- and skin-care preparations generally contain, above all, oil components and water. The oil components (emollients) used include, for example, hydrocarbons, ester oils and vegetable and animal oils/fats/waxes. In order to satisfy stringent market requirements in regard to sensory properties and optimal dermatological compatibility, new oil components and emulsifier mixtures are being continuously developed and tested. The use of ester oils in cosmetic products has been known for some time. Because of their importance, new processes for their production are also being continuously developed. Branched ester oils in particular impart a "lighter" skin feel and are therefore the subject of intensive research. The use of 2-methyl-1,3-propanediol monoesters is described, for example, in DE 101 60 681; the use of 2-methyl-1,3-propanediol diesters is described in DE 101 60 682. U.S. Pat. No. 2,921,089 describes di-(2-propylheptyl)-phthalate and its suitability as a plasticizer for PVC. EP 1 415 978 A1 (Oxeno Olefinchemie GmbH) describes mixtures containing benzoic acid-2-propylheptyl ester and the use of these mixtures as plasticizers for polymers, PVC or PVC plastisols and also their use in paints and lacquers, adhesives, adhesive components and sealing compounds.

The problem addressed by the present invention was to provide new ester oils preferably liquid at 20° C. for cosmetic applications which would have an improved profile in regard to their sensory properties (lightness, non-greasy skin feel, softness, spreadability, absorption, distribution behavior, oiliness) and which could be incorporated in a number of cosmetic formulations. The hydrolysis stability of the esters and their capacity for formulation at low pH values would also be of interest in this regard. In addition, the esters would lend themselves to incorporation both in w/o and in o/w formulations and would be compatible in particular with crystalline UV filters, pigments, antiperspirants, salts and silicones. It has surprisingly been found that esters of 2-propylheptanol lead to sensorially light products. Some of these esters and their production are known from DE 103 05 562, but for a totally different application, namely as polymer additives. WO 2006/097235 describes esters of 2-propylheptanol with linear or branched carboxylic acids. Unfortunately, these esters are problematic in the formulation of preparations containing UV filters. Above all, the unsatisfactory solubility of the UV filters is a limiting factor.

Accordingly, the problem addressed by the present invention was to provide esters that would be improved in relation to the prior art, more particularly esters which could readily be formulated together with UV filters and, at the same time, would not have any disadvantages relative to the prior art in regard to sensory impression.

DESCRIPTION OF THE INVENTION

The present invention relates to the use of esters of 2-propylheptanol with benzoic acid and/or benzoic acid derivatives in cosmetic and/or pharmaceutical preparations.

Surprisingly, esters propyl-branched in the alkyl chain are particularly suitable for cosmetic formulations, more particularly for formulations expected to impart a "light" skin feel. The esters can be incorporated particularly well in various formulations. Liquid substance mixtures are obtained and may be used accordingly as oil components or consistency factors according to chain length, branching and number of double bonds. According to the invention, a single 2-propylheptyl ester or a mixture of various esters may be used.

The present invention relates in particular to the use of esters of 2-propylheptanol with benzoic acid and/or benzoic acid derivatives in cosmetic and/or pharmaceutical preparations for wetting or impregnating or coating utility and/or hygiene wipes used for cleaning and/or care of the body.

A preferred embodiment of the invention is characterized by the use of esters with a total of 24 or fewer carbon atoms, preferably 22 or fewer carbon atoms.

The invention encompasses both the use of individual esters of 2-propylheptanol with benzoic acid and/or benzoic acid derivatives and the use of mixtures containing at least one of these esters.

According to the invention, esters of 2-propylheptanol with benzoic acid and/or benzoic acid derivatives . . . . Benzoic acid derivatives in the context of the invention are any compounds derived from benzoic acid, the —COOH group remaining unchanged (because it has to be available for the esterification with 2-propylheptanol).

Suitable benzoic acid derivatives are carboxy-substituted benzoic acids. The term "carboxy-substituted" is used synonymously with "carboxylated" and denotes benzoic acids which carry at least one other —COOH group. Suitable carboxy-substituted benzoic acids are mono- or di-carboxysubstituted benzoic acids.

Monocarboxy-substituted benzoic acids (=benzene dicarboxylic acids) are, for example, 1,2-benzene dicarboxylic acid (phthalic acid), 1,3-benzene dicarboxylic acid (isophthalic acid or m-phthalic acid), 1,4-benzenedicarboxylic acid (terephthalic acid).

Dicarboxy-substituted benzoic acids (=benzene tricarboxylic acids) are, for example, 1,2,3-benzene tricarboxylic acid (=hemimellitic acid), 1,2,4-benzene tricarboxylic acid (=trimellitic acid), 1,3,5-benzene tricarboxylic acid.

Tricarboxy-substituted benzoic acids (=benzene tetracarboxylic acids) are, for example 1,2,4,5-benzene tetracarboxylic acid (=pyromellitic acid).

The carboxysubstituted benzoic acids may optionally be alkyl- or hydroxyl-substituted.

Suitable benzoic acid derivatives are alkyl-substituted benzoic acids. The term "alkyl-substituted" is used synonymously with "alkylated" and denotes benzoic acids which carry at least one other substituent R on the benzene ring, the substituents R (independently of one another) representing a linear or branched, saturated or unsaturated alkyl group containing 1 to 8 carbon atoms. Suitable substituents R are, for example, methyl, ethyl, propyl-, isopropyl [=1-methylethyl-], propenyl-, isobutyl [2-methylpropyl], sec.butyl [=1-methylpropyl], tert.butyl [1,1-dimethylethyl], but-2-enyl, but-3-enyl, but-1-enyl, n-pentyl, 1-methylbutyl-, 2-methylbutyl-, 3-methylbutyl, 1-ethylpropyl, 1,1-dimethylpropyl, 1,2-dimethylpropyl, 2,2-dimethylpropyl, 1-pentenyl-, 2-pentenyl-, 3-pentenyl-, 4-pentenyl-, hexyl-, 1-methylpentyl-, 2-methylpentyl, 3-methylpentyl, 4-methylpentyl, 1-ethylbutyl-, 2-ethylbutyl-, 3-ethylbutyl-, 1-hexenyl, 2-hexenyl, 3-hexenyl, 4-hexenyl-, 5-hexenyl, heptyl, 1-methylhexyl-, 2-methylhexyl-, 3-methylhexyl-, 4-methylhexyl-, 5-methylhexyl, 1-hepentyl, 2-heptenyl, 3-heptenyl-, 4-heptenyl-, 5-heptenyl, 6-heptenyl-, n-octyl, 2-ethylhexyl-,1,1,3,3-tetramethylbutyl.

Examples of monoalkyl-substituted benzoic acids are methylbenzoic acids, such as 2-methylbenzoic acid (=o=toluoylic acid), 3-methylbenzoic acid (=m-toluoylic acid), 4-methylbenzoic acid (=p-toluoylic acid) or ethylbenzoic acids, such as 2-ethylbenzoic acid, 3-ethylbenzoic acid or 4-ethylbenzoic acid. Examples of polyalkyl-substituted benzoic acids are 2,4-dimethylbenoic acid, 2,3-dimethylbenzoic acid, 2,5-dimethylbenzoic acid, 2,6-dimethylbenzoic acid or 2,4,5-trimethylbenzoic acid. The polyalkyl-substituted benzoic acid derivatives of course also include those in which the alkyl groups R are not identical, for example 2-methyl-4-ethylbenzoic acid.

Other suitable benzoic acid derivatives are hydroxy-substituted benzoic acids. The term "hydroxy-substituted" is used synonymously with "hydroxylated" and denotes benzoic acids which carry at least one other group —OH on the benzene ring. Examples of monohydroxy-substituted benzoic acids are 2-hydroxybenzoic acid (salicylic acid), 3-hydroxybenzoic acid, 4-hydroxybenzoic acid. Examples of polyhydroxy-substituted benzoic acids are 2,4-dihydroxybenzoic acid and 2,5-dihydroxybenzoic acid.

Other suitable benzoic acid derivatives are hydroxy- and alkyl-substituted benzoic acids. Hydroxy- and alkyl-substituted benzoic acids are benzoic acids which carry at least one —OH group on the benzene ring and at least one alkyl group R (as defined above for the alkyl-substituted benzoic acids). Examples of hydroxy- and alkyl-substituted benzoic acids are 2-methyl-3-hydroxybenzoic acid and 2-ethyl-3-hydroxybenzoic acid.

Other suitable benzoic acid derivatives are derivatives obtainable by acylation of hydroxy-substituted benzoic acids such as, for example, acetylsalicylic acid. The acyl group inserted by acylation can have, for example, the following formula: —C(=O)—$R_1$, where $R_1$ is a linear or branched, saturated or unsaturated alkyl group containing 1 to 8 carbon atoms.

In a preferred embodiment of the invention, compounds selected from the group consisting of methyl-substituted benzoic acids, hydroxy-substituted benzoic acids, carboxy-substituted benzoic acids, derivatives obtainable by acylation of hydroxy-substituted benzoic acids are used as benzoic acid derivatives.

The expression "esters of 2-propylheptanol with benzene dicarboxylic acids" encompasses both diesters of benzene dicarboxylic acid with 2-propylheptanol, i.e. for example di-2-propylheptyl-1,4-benzenedicarboxylic acid diester [di-2-propylheptyl terephthalic acid], and monoesters, such as for example 2-propylheptyl-1,4-benzenedicarboxylic acid ester, in which only one acid group of the benzene dicarboxylic acid is esterified and in which the second acid group is free. It also encompasses mixed esters in which one acid group of the benzene dicarboxylic acid is esterified with 2-propylheptanol and the second acid group is esterified with another alcohol. One embodiment of the invention is characterized by the use of mixed esters of benzene dicarboxylic acids (more particularly benzene-1,4-dicarboxylic acids) and 2-propylheptanol and another alcohol selected from the group consisting of 3-methyl-2-propylhexanol, 4-methyl-2-propylhexanol and 5-methyl-2-propylhexanol.

In one embodiment of the invention, the mixed esters are obtained by reaction of the corresponding benzene dicarboxylic acid with a mixture of 2-propylheptanol, 3-methyl-2-propylhexanol, 4-methyl-2-propylhexanol and 5-methyl-2-propylhexanol.

Another embodiment is characterized by the use of mixed esters of benzene dicarboxylic acids and 2-propyl heptanol and another alcohol with the general formula R—OH, where R is a linear or branched, saturated or unsaturated alkyl group containing 1 to 12 carbon atoms.

Another embodiment is characterized by the use of mixed esters of benzene dicarboxylic acids and 2-propyl heptanol and another alcohol with the general formula R—OH, where R is a saturated, linear or branched alkyl group containing 1 to 12 carbon atoms.

Another preferred embodiment is characterized by the use of mixed esters of benzene dicarboxylic acids and 2-propyl heptanol and another alcohol, the other alcohol being selected from the group consisting of methanol, ethanol, propanol, isopropanol, butanol, isobutanol, pentanol, hexanol, isohexanol, octanol, decanol or dodecanol.

The present invention also relates to esters of 2-propylheptanol with benzoic acid derivatives excluding di-[2-propylheptyl]-1,2-benzenedicarboxylic acid ester.

In another preferred embodiment of the invention, compounds selected from the group consisting of methyl-substituted benzoic acids, hydroxy-substituted benzoic acid, carboxy-substituted benzoic acids, derivatives obtainable by acylation of hydroxy-substituted benzoic acids are used as benzoic acid derivatives.

A preferred embodiment of the invention relates to esters selected from the group consisting of di-[2-propylheptyl]-1,4-benzene dicarboxylic acid diester, 2-propylheptyl-1,4-benzene dicarboxylic acid ester, 2-propylheptyl-2-hydroxybenzoic acid ester, 2-propylheptyl-2-methylbenzoic acid ester, 2-propylheptyl-3-methylbenzoic acid ester, 2-propylheptyl-4-methylbenzoic acid ester, 2-propylheptyl-2-acetoxybenzoic acid ester (=2-propylheptyl acetyl salicylic acid ester).

The invention encompasses both individual esters and mixtures of various esters.

The present invention relates to compositions containing an ester of 2-propylheptanol with benzoic acid derivatives and at least one other ester of the same benzoic acid derivative with an alcohol selected from the group consisting of 3-methyl-2-propylhexanol, 4-methyl-2-propyl hexanol or 5-methyl-2-propyl hexanol.

In a preferred embodiment of the invention, these compositions contain
80 to 99.99% by weight of the 2-propylheptyl ester,
0.01 to 20% by weight of the corresponding methyl-2-propylhexyl ester.

These compositions are suitable in cosmetic and/or pharmaceutical preparations.

The invention also relates to a process for the production of the esters according to the invention, in which a mixture containing 2-propyl heptanol and the corresponding benzoic acid derivative are reacted.

The process according to the invention also encompasses the production of ester mixtures in which 2-propylheptanol is reacted together with the corresponding benzoic acid derivative mixture.

The process according to the invention also encompasses the production of compositions according to claim 5, in which a mixture of 2-propyl heptanol and at least one alcohol selected from the group consisting of 3-methyl-2-propylhexanol, 4-methyl-2-propylhexanol or 5-methyl-2-propylheptanol and the corresponding benzoic acid derivative are reacted.

In a preferred embodiment of the invention, the mixture containing alcohol and the corresponding benzoic acid derivative is reacted in the presence of an esterification catalyst.

In a preferred embodiment, the mixture containing alcohol and the corresponding benzoic acid is heated, the water formed is continuously removed and the crude product is distilled. The process may be carried out in the presence of an esterification catalyst, for example an acid or a base. In a preferred embodiment, the process is carried out in the absence of solvents, preferably with educts which are substantially water-free. A preferred embodiment of the process is characterized by the use of a tin catalyst. Suitable tin catalysts are, for example, tin oxalate (for example Fascat® 2001), tin oxide (SnO, Fascat® 2000) and tin(IV) catalysts, such as dibutyl tin diacetate (Fascat® 4200), dibutyl tin oxide (Fascat® 4201) and dibutyl tin laurate (Fascat® 4202) or tin oxide (SnO) which were once marketed by Atofina, but are now marketed by Arkema.

The esterification is preferably carried out at temperatures in the range from 100 to 300° C. and, more particularly, at temperatures in the range from 200 to 250° C.

In another embodiment, at least one enzyme is used as the catalyst. Suitable enzymes are any enzymes or enzyme mixtures known to the expert which are capable of catalyzing the esterification of alcohol and acid, for example lipases, acyl transferases and esterases. The enzyme-catalyzed esterification is typically carried out at temperatures of 20 to 100° C. and preferably at temperatures of 40 to 80° C.

The present invention also relates to a process for the production of the esters according to the invention, in which a mixture containing 2-propylheptanol and the methyl ester of the corresponding benzoic acid derivative is reacted in the presence of a transesterification catalyst.

The process according to the invention also encompasses the production of ester mixtures, in which 2-propylheptanol is reacted together with the corresponding mixtures of the methyl esters of the corresponding benzoic acid derivatives acids in the presence of an esterification catalyst.

The process according to the invention also encompasses the production of the compositions claimed in claim 5, in which a mixture of 2-propylheptanol and at least one alcohol selected from the group consisting of 3-methyl-2-propylhexanol, 40methyl-2-propylhexanol or 5-methyl-2-propylhexanol and the methyl ester of the corresponding benzoic acid derivative is reacted in the presence of a transesterification catalyst.

In a preferred embodiment, the mixture containing alcohol and the methyl ester of the corresponding benzoic acid derivative is heated in the presence of the esterification catalyst, the water formed is continuously removed and the crude product is distilled. In a preferred embodiment, the process is carried out in the absence of solvents, preferably with educts which are substantially water-free.

The esterification is preferably carried out at temperatures of 100 to 300° C. and more particularly at temperatures of 200 to 250° C. The transesterification catalyst may be selected from any of the transesterification catalysts known to the expert, sodium methylate or tetra-alkyl titanate preferably being used.

In another embodiment, at least one enzyme is used as the catalyst. Suitable enzymes are any enzymes or enzyme mixtures known to the expert which are capable of catalyzing the transesterification of alcohol and acid methyl ester, for example lipases, acyl transferases and esterases. The enzyme-catalyzed esterification is typically carried out at temperatures of 20 to 100° C. and preferably at temperatures of 40 to 80° C.

The expressions "esters of X-methyl-2-propylhexanol with benzene dicarboxylic acids" used in the following encompass both diesters of the benzene dicarboxylic acids with the particular methyl-2-propylhexanol, i.e. for example di-3-methyl-2-propylhexyl-1,4-benzene dicarboxylic acid diester or di-5-methyl-2-propylhexyl-1,4-benzene dicarboxylic acid diester, and also monoesters, such as for example 3-methyl-2-propylheptyl-1,4-benzene dicarboxylic acid monoester, and mixed esters in which one acid group of the benzene dicarboxylic acid is esterified with the particular methyl-2-propylhexanol and the second acid group of the benzene dicarboxylic acid is esterified with a second alcohol. The second alcohol may be selected from 3-methyl-2-propylhexanol, 4-methyl-2-propylhexanol and 5-methyl-2-propylhexanol, the second alcohol having to be different from the first methyl-2-propylhexanol. In another embodiment of the mixed esters, the second alcohol is selected from the group consisting of methanol, ethanol, propanol, isopropanol, butanol, isobutanol, pentanol, hexanol, isohexanol, octanol, decanol and dodecanol.

Esters of 3-methyl-2-Propylhexanol with Benzoic Acid and/or Benzoic Acid Derivatives The present invention also relates to esters of 3-methyl-2-propylhexanol with benzoic acid and/or benzoic acid derivatives and to their use in cosmetic and/or pharmaceutical preparations.

One embodiment of the invention is 3-methyl-2-propylhexyl benzoic acid. Another embodiment of the invention is di-[3-methyl-2-propylhexyl]-1,4-benzoic acid diester.

Esters of 4-methyl-2-Propylhexanol with Benzoic Acid and/or Benzoic Acid Derivatives The present invention also relates to esters of 4-methyl-2-propylhexanol with benzoic acid derivatives.

The present invention also relates to the use of esters of 4-methyl-2-propylhexanol with benzoic acid and/or benzoic acid derivatives in cosmetic and/or pharmaceutical preparations.

One embodiment of the invention is di-[4-methyl-2-propylhexyl]-1,4-benzoic acid diester.

Esters of 5-methyl-2-Propylhexanol with Benzoic Acid and/or Benzoic Acid Derivatives The present invention also relates to esters of 5-methyl-2-propylhexanol with benzoic acid derivatives.

The present invention also relates to the use of esters of 5-methyl-2-propylhexanol with benzoic acid and/or benzoic acid derivatives in cosmetic and/or pharmaceutical preparations.

One embodiment of the invention is di-[5-methyl-2-propylhexyl]-1,4-benzoic acid diester.

The present invention also relates to a process for the production of esters of 3-methyl-2-propylhexanol with benzoic acid and/or benzoic acid derivatives, in which a mixture containing 3-methyl-2-propylhexanol and the corresponding acid (carboxylic acid and/or dicarboxylic acid) is reacted. The process according to the invention also encompasses the production of ester mixtures, in which 3-methyl-2-propylhexanol is reacted together with the corresponding acid mixtures. The process according to the invention also encompasses the production of mixed esters, in which 3-methyl-2-propylhexanol and another alcohol are reacted together with the corresponding dicarboxylic acid.

The present invention also relates to a process for the production of esters of 4-methyl-2-propylhexanol with benzoic acid derivatives, in which a mixture containing 4-methyl-2-propylhexanol and the corresponding acid (carboxylic acid and/or dicarboxylic acid) is reacted. The process according to the invention also encompasses the production of ester mixtures, in which 4-methyl-2-propylhexanol is reacted together with the corresponding acid mixtures. The process according to the invention also encompasses the production of mixed esters, in which 4-methyl-2-propylhexanol and another alcohol are reacted together with the corresponding dicarboxylic acid.

The present invention also relates to a process for the production of esters of 5-methyl-2-propylhexanol with benzoic acid derivatives, in which a mixture containing 5-methyl-2-propylhexanol and the corresponding acid (carboxylic acid and/or dicarboxylic acid) is reacted. The process according to the invention also encompasses the production of ester mixtures, in which 5-methyl-2-propylhexanol is reacted together with the corresponding acid mixtures. The process according to the invention also encompasses the production of mixed esters, in which 5-methyl-2-propylhexanol and another alcohol are reacted together with the corresponding dicarboxylic acid.

In a preferred embodiment of the invention, the mixture containing alcohol (5-methyl-2-propylhexanol, 4-methyl-2-propylhexanol and/or 3-methyl-2-propylhexanol or the other alcohol, if any) and the corresponding acid is reacted in the presence of an esterification catalyst.

In a preferred embodiment of the invention, the mixture containing alcohol (5-methyl-2-propylhexanol, 4-methyl-2-propylhexanol and/or 3-methyl-2-propylhexanol or the other alcohol, if any) and the corresponding acid is heated, the water formed is continuously removed and the crude product is then distilled. The process may be carried out in the presence of an esterification catalyst, for example an acid or a base. In a preferred embodiment, the process is carried out in the absence of solvents, preferably with educts which are substantially water-free. A preferred embodiment of the process is characterized by the use of a tin catalyst. Suitable tin catalysts are, for example, tin oxalate (for example Fascat® 2001), tin oxide (SnO, Fascat® 2000) and tin(IV) catalysts, such as dibutyl tin diacetate (Fascat® 4200), dibutyl tin oxide (Fascat® 4201) and dibutyl tin laurate (Fascat® 4202) or tin oxide (SnO) which were once marketed by Atofina, but are now marketed by Arkema.

The esterification is preferably carried out at temperatures in the range from 100 to 300° C. and, more particularly, at temperatures in the range from 200 to 250° C.

In another embodiment, at least one enzyme is used as the catalyst. Suitable enzymes are any enzymes or enzyme mixtures known to the expert which are capable of catalyzing the esterification of alcohol and acid, for example lipases, acyl transferases and esterases. The enzyme-catalyzed esterification is typically carried out at temperatures of 20 to 100° C. and preferably at temperatures of 40 to 80° C.

The present invention also relates to a process for the production of esters of 3-methyl-2-propylhexanol with benzoic acid and/or benzoic acid derivatives, in which a mixture containing 3-methyl-2-propylhexanol and the methyl ester of the corresponding acid is reacted in the presence of a transesterification catalyst. The process according to the invention also encompasses the production of mixed esters, in which 3-methyl-2-propylhexanol and another alcohol are reacted together with the methyl or dimethyl ester of the corresponding dicarboxylic acid in the presence of a transesterification catalyst.

The present invention also relates to a process for the production of esters of 4-methyl-2-propylhexanol with benzoic acid derivatives, in which a mixture containing 4-methyl-2-propylhexanol and the methyl ester of the corresponding acid is reacted in the presence of a transesterification catalyst. The process according to the invention also encompasses the production of mixed esters, in which 4-methyl-2-propylhexanol and another alcohol are reacted together with the methyl or dimethyl ester of the corresponding dicarboxylic acid in the presence of a transesterification catalyst.

The present invention also relates to a process for the production of esters of 5-methyl-2-propylhexanol with benzoic acid derivatives, in which a mixture containing 5-methyl-2-propylhexanol and the methyl ester of the corresponding acid is reacted in the presence of a transesterification catalyst. The process according to the invention also encompasses the production of mixed esters, in which 5-methyl-2-propylhexanol and another alcohol are reacted together with the methyl or dimethyl ester of the corresponding dicarboxylic acid in the presence of a transesterification catalyst. The process according to the invention also encompasses the production of ester mixtures, in which the alcohol (5-methyl-2-propylhexanol, 4-methyl-2-propylhexanol, 3-methyl-2-propylhexanol) is reacted together with the corresponding mixtures of the methyl esters of the acids in the presence of a transesterification catalyst.

In a preferred embodiment, the mixture containing alcohol (5-methyl-2-propylhexanol, 4-methyl-2-propylhexanol, 3-methyl-2-propylhexanol) and the methyl ester of the corresponding acid is heated in the presence of the esterification catalyst, the water formed is continuously removed and the crude product is distilled. In a preferred embodiment, the process is carried out in the absence of solvents, preferably with educts which are substantially water-free.

The esterification is preferably carried out at temperatures of 100 to 300° C. and more particularly at temperatures of 200 to 250° C. The transesterification catalyst used may be selected from any of those known to the expert, sodium methylate or tetra-alkyl titanate being preferred.

In another embodiment, at least one enzyme is used as the catalyst. Suitable enzymes are any enzymes or enzyme mixtures known to the expert which are capable of catalyzing the transesterification of alcohol and acid methyl ester, for example lipases, acyl transferases and esterases. The enzyme-catalyzed esterification is typically carried out at temperatures of 20 to 100° C. and preferably at temperatures of 40 to 80° C.

Cosmetic/Pharmaceutical Preparations

The 2-propylheptyl esters of benzoic acid and/or benzoic acid derivatives allow the production of stable cosmetic and pharmaceutical emulsions with a particularly light skin feel.

Accordingly, the present invention also relates to cosmetic and/or pharmaceutical preparations containing
(a) at least one ester of 2-propylheptanol with benzoic acid and/or benzoic acid derivatives
(b) at least one emulsifier and/or surfactant and/or wax component and/or polymer and/or another oil component.

The preparations according to the invention preferably contain 0.1 to 80% by weight, more particularly 0.5 to 70% by weight, preferably 0.75 to 60% by weight, more particularly 1 to 50% by weight, preferably 1 to 40% by weight of at least one ester of 2-propylheptanol with benzoic acid and/or benzoic acid derivatives.

The present invention also relates to cosmetic and/or pharmaceutical preparations containing
(a) 0.1 to 80% by weight, more particularly 0.1 to 70% by weight, preferably 0.1 to 60% by weight, more particularly 0.1 to 50% by weight, preferably 0.1 to 40% by weight of at least one ester of 2-propylheptanol with benzoic acid and/or benzoic acid derivatives,
b) 0.1 to 20% by weight of emulsifier (b-1) and/or surfactant (b-2) and/or wax component (b-3) and/or polymer (b-4), 0.1 to 40% by weight of other oil components (b-5) and
c) 0 to 98% by weight of water.

The preparations according to the invention contain at least 0.1, more particularly at least 0.5, more particularly at least 0.75, preferably at least 1, preferably at least 5% by weight of one or more esters (a).

All percentages by weight represent % by weight, based on the cosmetic and/or pharmaceutical preparation.

In one embodiment of the invention, the preparations contain at least one ester selected from the group consisting of 2-propylheptyl benzoic acid ester, di-[2-propylheptyl]-1,4-benzene dicarboxylic acid diester, 2-propylheptyl-1,4-benzene dicarboxylic acid ester, 2-propylheptyl-2-hydroxybenzoic acid ester, 2-propylheptyl-2-methylbenzoic acid ester, 2-propylheptyl-3-methylbenzoic acid ester, 2-propylheptyl-4-methylbenzoic acid ester, 2-propylheptyl-2-acetoxybenzoic acid ester (=2-propylheptyl acetyl salicylic acid ester).

Another preferred embodiment of the cosmetic and/or pharmaceutical preparations contains (a) 0.1 to 80, more particularly 0.1 to 70, preferably 0.1 to 60, preferably 0.1 to 50% by weight of at least one ester of 2-propylheptanol with benzoic acid and/or benzoic acid derivatives, (b) 0.1 to 20% by weight of emulsifiers (b-1) and/or surfactants (b-2) and/or wax components (b-3) and/or polymers (b-4) and 0.1 to 40% by weight of other oil components (b-5) and (c) 0 to 98% by weight of water.

The present invention also relates to cosmetic and/or pharmaceutical preparations containing
(a) at least one ester of 3-methyl-2-propylhexanol with benzoic acid and/or benzoic acid derivatives
(b) at least one emulsifier and/or surfactant and/or wax component and/or polymer and/or another oil component.

The present invention also relates to cosmetic and/or pharmaceutical preparations containing
(a) at least one ester of 4-methyl-2-propylhexanol with benzoic acid and/or benzoic acid derivatives
(b) at least one emulsifier and/or surfactant and/or wax component and/or polymer and/or another oil component.

The present invention also relates to cosmetic and/or pharmaceutical preparations containing
(a) at least one ester of 5-methyl-2-propylhexanol with benzoic acid and/or benzoic acid derivatives
(b) at least one emulsifier and/or surfactant and/or wax component and/or polymer and/or another oil component.

The preparations according to the invention, the compositions according to the invention and the esters according to the invention are suitable for incorporation as a base in all cosmetic body care and cleansing preparations such as, for example, body oil, baby oil, body milk, creams, lotions, sprayable emulsions, sunscreens, antiperspirants, liquid and bar soaps, etc. They may also be used in surfactant-containing formulations such as, for example, foam and shower baths, hair shampoos and hair care rinses. They may be applied as a care component to tissues, papers, wipes, nonwovens, sponges, puffs, plasters and bandages which are used in the field of hygiene and care (wet wipes for baby hygiene and baby care, cleaning wipes, facial wipes, skin care wipes, care wipes containing active ingredients against ageing of the skin, wipes containing sun protection formulations and insect repellents and wipes for decorative cosmetics or for after-sun treatment, toilet wipes, antiperspirant wipes, diapers, handkerchiefs, wet wipes, hygiene products, self-tanning wipes). They may also be used linter alia in hair-care, hair-cleaning or hair-coloring preparations.

Depending on the application envisaged, the cosmetic formulations contain a number of other auxiliaries and additives such as, for example, surfactants, other oil components, emulsifiers, pearlizing waxes, consistency factors, thickeners, superfatting agents, stabilizers, polymers, fats, waxes, lecithins, phospholipids, biogenic agents, UV protection factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, etc. which are listed by way of example in the following.

Emulsifier b-1

In one embodiment of the invention, the preparations according to the invention contain at least one emulsifier. The compositions according to the invention contain(s) the emulsifier(s) in a quantity of 0 to 40% by weight, preferably 0.1 to 20% by weight, preferably 0.1 to 15% by weight and more particularly 0.1 to 10% by weight, based on the total weight of the composition.

In one embodiment of the invention, the preparation according to the invention contains more than one emulsifier. Depending on the other components, the expert uses typical emulsifier systems (such as, for example, emulsifier and co-emulsifier).

Nonionic Emulsifiers

The group of nonionic emulsifiers includes, for example,
(1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;
(2) $C_{12-18}$ fatty acid monoesters and diesters of products of the addition of 1 to 50 mol ethylene oxide onto glycerol;
(3) sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) products of the addition of 7 to 60 mol ethylene oxide onto castor oil and/or hydrogenated castor oil;
(6) polyol esters and, in particular, polyglycerol esters such as, for example, polyolpoly-12-hydroxystearate, polyglycerol polyricinoleate, polyglycerol diisostearate or polyglycerol dimerate. Mixtures of compounds from several of these classes are also suitable;
(7) products of the addition of 2 to 15 mol ethylene oxide onto castor oil and/or hydrogenated castor oil;

(8) partial esters based on linear, branched, unsaturated or saturated $C_{6-22}$ fatty acids, ricinoleic acid and 12-hydroxystearic acid and polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) or mixed esters, such as glyceryl stearate citrate and glyceryl stearate lactate for example;

(9) polysiloxane/polyalkyl polyether copolymer or corresponding derivatives;

(10) mixed esters of pentaerythritol, fatty acids, citric acid and fatty alcohol and/or mixed esters of fatty acids containing 6 to 22 carbon atoms, methyl glucose and polyols, preferably glycerol or polyglycerol.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. These emulsifiers are w/o or o/w emulsifiers, depending on the degree of ethoxylation. $C_{12/18}$ fatty acid monoesters and diesters of addition products of ethylene oxide onto glycerol are known as lipid layer enhancers for cosmetic preparations.

According to the invention, particularly suitable and mild emulsifiers are the polyol poly-12-hydroxystearates and mixtures thereof marketed by Cognis Deutschland GmbH under the name of "Dehymuls® PGPH" (w/o emulsifier) or "Eumulgin® VL 75" (mixture with Coco Glucosides in a ratio by weight of 1:1, o/w emulsifier) or "Dehymuls® SBL" (w/o emulsifier). Particular reference is made in this connection to EP 0 766 661 B1. The polyol component of these emulsifiers may be derived from substances which contain at least two, preferably 3 to 12 and more particularly 3 to 8 hydroxyl groups and 2 to 12 carbon atoms.

In principle, suitable lipophilic w/o emulsifiers are emulsifiers with an HLB value of 1 to 8 which are listed in numerous Tables and are well-known to the expert. Some of these emulsifiers are listed, for example, in Kirk-Othmer, "Encyclopedia of Chemical Technology", 3rd Edition, 1979, Vol. 8, page 913. The HLB value for ethoxylated products may also be calculated to the following formula: HLB=(100-L): 5, where L is the percentage by weight of lipophilic groups, i.e. fatty alkyl or fatty acyl groups, in percent by weight in the ethylene oxide adducts.

Of particular advantage from the group of w/o emulsifiers are partial esters of polyols, more particularly $C_{4-6}$ polyols, such as for example partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxy-stearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

Depending on the formulation, it can also be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example 10-20 ethylene oxide units for o/w emulsifiers and 20-40 ethylene oxide units for so-called solubilizers. Particularly advantageous o/w emulsifiers for the purposes of the invention are Ceteareth-12 and PEG-20 Stearate. Particularly suitable solubilizers are Eumulgin® HRE 40 (INCI name: PEG-40 Hydrogenated Castor oil), Eumulgin® HRE 60 (INCI name: PEG-60 Hydrogenated Castor Oil), Eumulgin® L (INCI name: PPG-1-PEG-9 Laurylglycolether) and Eumulgin® SML 20 (INCI name: Polysorbat-20).

Nonionic emulsifiers from the group of alkyl oligoglycosides are particularly compatible with the skin. $C_{8-22}$ alkyl mono- and oligoglycosides, their production and their use are known from the prior art. They are produced in particular by reacting glucose or oligosaccharides with primary alcohols containing 8 to 22 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based. Products available under the name of Plantacare® contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the name of Emulgade® PL 68/50 by Cognis Deutschland GmbH, which is a 1:1 mixture of alkyl polyglucosides and fatty alcohols, is preferred for the purposes of the invention. According to the invention, the mixture of Lauryl Glucoside, Polyglyceryl-2-Dipolyhydroxystearate, glycerol and water which is marketed as Eumulgin® VL 75 may also be used with advantage in accordance with the invention.

Other suitable emulsifiers are such substances as lecithins and phospholipids. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are generally classed as fats. Sphingosines and sphingolipids are also suitable as fatlike substances.

Surfactants b-2)

In one embodiment of the invention, the preparations according to the invention contain at least one surfactant. The surfactant(s) may be selected from anionic, nonionic, cationic and/or amphoteric or zwitterionic surfactants. Surfactant-containing cosmetic preparations, such as for example shower gels, foam baths, shampoos, etc., preferably contain at least one anionic surfactant.

The compositions according to the invention contain the surfactant(s) in a quantity of 0 to 40% by weight, preferably 0 to 20% by weight, preferably 0.1 to 15% by weight and more particularly 0.1 to 10% by weight, based on the total weight of the composition.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid- N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_{8-18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylamino-butyric acids, N-alkyliminodipropionic acids, N-hydroxyethyl-N-alkyl-amidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the expert in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12-18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

Wax Component b-3)

In one embodiment of the invention, the preparations according to the invention contain at least one wax component. The compositions according to the invention contain the wax component(s) in a quantity of 0 to 40% by weight, more particularly 0 to 20% by weight, preferably 0.1 to 15% by weight and more particularly 0.1 to 10% by weight, based on the total weight of the composition.

Waxes are normally understood to be natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. A single wax component or a mixture of wax components melting at or above 30° C. may be used in accordance with the invention.

According to the invention, fats and fat-like substances with a wax-like consistency may also be used as waxes providing they have the required melting point. These include inter alia fats (triglycerides), mono- and diglycerides, natural and synthetic waxes, fat and wax alcohols, fatty acids, esters of fatty alcohols and fatty acids and fatty acid amides or mixtures of these substances.

Fats in the context of the invention are understood to be triacylglycerols, i.e. the triple esters of fatty acids with glycerol. The triacylglycerols preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina® HR. Glycerol tristearate, glycerol tribehenate (for example Syncrowax® HRC), glycerol tripalmitate or the triglyceride mixtures known under the name of Syncrowax® HGLC are also suitable providing the melting point of the wax component or the mixture is 30° C. or higher.

According to the invention, suitable wax components are, in particular, mono- and diglycerides and mixtures of these partial glycerides. Glyceride mixtures suitable for use in accordance with the invention include the products Novata® AB and Novata® B (mixture of $C_{12-18}$ mono-, di- and triglycerides) and Cutina® MD or Cutina® GMS (glyceryl stearate) marketed by Cognis Deutschland GmbH & Co. KG.

The fatty alcohols suitable for use as a wax component in accordance with the invention include $C_{12-50}$ fatty alcohols. The fatty alcohols may be obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated unbranched fatty alcohols are preferred. However, unsaturated, branched or unbranched fatty alcohols may also be used as the wax component in accordance with the invention providing they have the required melting point. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols) or the partly branched alcohols from the oxosynthesis (Dobanols) may also be used. $C_{14-22}$ fatty alcohols marketed for example by Cognis Deutschland GmbH under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are particularly suitable for the purposes of the invention. Fatty alcohols give the compositions a dryer feeling on the skin than triglycerides.

$C_{14-40}$ fatty acids or mixtures thereof may also be used as wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes suitable for use in accordance with the invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Examples of esters such as these include, for example, $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. Other suitable wax components which may be used are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

Polymers b-4)

In one embodiment of the invention, the preparations according to the invention contain at least one polymer. The compositions according to the invention contain the polymer(s) in a quantity of 0 to 20% by weight, preferably 0.1 to 15% by weight and, more particularly, 0.1 to 10% by weight, based on the total weight of the composition.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Other suitable polymers are polysaccharides, more particularly xanthan gum, guar guar, agar agar, alginates and tyloses.

Other Oil Components b-5)

Body-care preparations, such as creams, body oils, lotions and milks, typically contain a number of other oil components and emollients which contribute towards further optimizing the sensory properties. The oil components (esters according to the invention plus other oil components) are typically present in a total quantity of 0.1 to 80, more particularly 0.5 to 70, preferably 1 to 60, more particularly 1 to 50% by weight, more particularly 1 to 40% by weight, preferably 5 to 25% by weight and more particularly 5 to 15% by weight. The other oil components are typically present in a quantity of 0.1 to 40% by weight.

The other oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol), triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols and hydrocarbons or mixtures thereof (Cetiol® DD).

Other Ingredients

Suitable thickeners are, for example, Aerosil® types (hydrophilic silicas), carboxymethyl cellulose and hydroxyethyl and hydroxypropyl cellulose, polyvinyl alcohol, polyvinyl pyrrolidone and bentonites, for example Bentone® Gel VS-5PC (Rheox).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. Typical UV-A filters are, in particular, derivatives of benzoyl methane. The UV-A and UV-B filters may of course also be used in the form of mixtures, for example combinations of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) and esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are often combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide. Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers.

Suitable insect repellents are N,N-diethyl-m-toluamide, pentane-1,2-diol or 3-(N-n-butyl-N-acetylamino)-propionic acid ethyl ester), which is marketed as Insect Repellent 3535 by Merck KGaA, and Butylacetyl-aminopropionate.

A suitable self-tanning agent is, for example, dihydroxyacetone. Suitable tyrosine inhibitors, which prevent the formation of melanin and are used in depigmenting agents, are, for example, arbutin, ferulic acid, koji acid, coumaric acid and ascorbic acid (vitamin C).

Suitable preservatives are, for example, phenoxyethanol, formal-dehyde solution, parabens, pentanediol or sorbic acid and the silver complexes known under the name of Surfacine® and the other classes of compounds listed in Appendix 6, Parts A and B of the Kosmetik-verordnung ("Cosmetics Directive").

Suitable perfume oils are mixtures of natural and synthetic perfumes. Natural perfumes are extracts of flowers, stems and leaves, fruits, fruit peel, roots, woods, herbs and grasses, needles and branches, resins and balsams. Also suitable are animal raw materials, for example civet and beaver, and synthetic perfume compounds of the ester, ether, aldehyde, ketone, alcohol and hydrocarbon type.

Suitable pearlizing waxes, particularly for use in surfactant-containing formulations, are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Metal salts of fatty acids such as, for example, magnesium, aluminium and/or zinc stearate or ricinoleate may be used as stabilizers.

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen.

The preparations according to the invention, the compositions according to the invention and the esters according to the invention are suitable, particularly in cosmetic and/or pharmaceutical preparations, for wetting or impregnating or coating utility and hygiene wipes which are used for care and/or cleansing of the body.

Examples of utility and hygiene wipes include tissues, papers, wipes, nonwovens, sponges, puffs, plasters and bandages which are used in the field of hygiene and care. These may be wet wipes for baby hygiene and baby care, cleaning wipes, facial wipes, skin care wipes, care wipes containing active ingredients against ageing of the skin, wipes containing sun protection formulations and insect repellents and wipes for decorative cosmetics or for after-sun treatment, toilet wipes, antiperspirant wipes, diapers, handkerchiefs, wet wipes, hygiene products and self-tanning wipes.

The invention claimed is:

1. A method of preparing cosmetic and/or pharmaceutical preparations comprising adding to a cosmetic and/or pharmaceutical base, at least one ester of 2-propylheptanol with benzoic acid and/or a benzoic acid derivative.

2. The method of claim 1, wherein the benzoic acid derivative is selected from the group consisting of methyl-substituted benzoic acids, hydroxy-substituted benzoic acids, carboxy-substituted benzoic acids, and derivatives obtained by acylation of hydroxy-substituted benzoic acids.

3. The method of claim 1, wherein the cosmetic and/or pharmaceutical preparation comprises a body oil, a baby oil, a body milk, a cream, a lotion, a sprayable emulsion, a sunscreen, an antiperspirant, or a liquid or bar soap.

4. The method of claim 1, further comprising wetting, impregnating or coating utility and/or hygiene wipes with the cosmetic and/or pharmaceutical preparation.

5. The method of claim 4, wherein the coating and/or utility wipes comprise one or more of tissues, papers, wipes, nonwovens, sponges, puffs, plasters and bandages.

6. The method of claim 1, wherein the ester comprises 24 or fewer carbon atoms.

7. The method of claim 1, wherein the ester comprises 22 or fewer carbon atoms.

* * * * *